(12) United States Patent
Davis

(10) Patent No.: US 8,187,489 B1
(45) Date of Patent: May 29, 2012

(54) BIODEGRADABLE IONIC LIQUIDS FOR AIRCRAFT DEICING

(75) Inventor: Matthew C. Davis, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/069,671

(22) Filed: Mar. 23, 2011

(51) Int. Cl.
C09K 3/18 (2006.01)
C07C 209/00 (2006.01)

(52) U.S. Cl. .............................. 252/70; 106/13; 564/293

(58) Field of Classification Search .................... 252/70; 106/13; 564/293
See application file for complete search history.

(56) References Cited

U.S. PATENT DOCUMENTS

| | | | |
|---|---|---|---|
| 6,294,104 B1 | 9/2001 | Ives et al. | |
| 6,573,405 B1 * | 6/2003 | Abbott et al. | 564/292 |
| 7,183,433 B2 * | 2/2007 | Abbott et al. | 564/282 |
| 7,196,221 B2 * | 3/2007 | Abbott et al. | 564/282 |
| 7,566,686 B2 * | 7/2009 | Kippie et al. | 507/260 |
| 7,718,036 B2 * | 5/2010 | Sumnicht et al. | 162/146 |
| 7,985,321 B2 * | 7/2011 | Sumnicht et al. | 162/146 |
| 2004/0054231 A1 * | 3/2004 | Abbott et al. | 564/282 |
| 2004/0097755 A1 * | 5/2004 | Abbott et al. | 562/553 |
| 2009/0236227 A1 * | 9/2009 | Kuzmanovic et al. | 205/80 |

OTHER PUBLICATIONS

Derwent-Acc-No. 2008-N69908, abstract of Chinese Patent Specification No. CN 101260051A (Sep. 2008).*

Nockemann, et al, K. Choline saccharinate and choline acesulfamate: ionic liquids with low toxicities. J. Phys. Chem. B 2007, 111, 5254-5263.

Carter, et al.. Sweet success: ionic liquids derived from non-nutritive sweetners. Chem. Commun. 2004, 630-631.

* cited by examiner

*Primary Examiner* — Anthony J Green

(74) *Attorney, Agent, or Firm* — Brian Drazich; Charlene Haley

(57) ABSTRACT

A process and deicing composition.

14 Claims, No Drawings

BIODEGRADABLE IONIC LIQUIDS FOR AIRCRAFT DEICING

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to an environmentally-friendly composition for use in the deicing of aircraft and runway surfaces.

DETAILED DESCRIPTION OF THE EMBODIMENTS OF THE INVENTION

Embodiments of the invention generally relate to an environmentally-friendly composition for use in the deicing of aircraft and runway surfaces.

The ionic liquids described herein are unique in that they are composed of naturally occurring ions and have low toxicity. Ionic liquids (ILs) with low toxicity are effective in melting ice from aircraft wings and fuselage surfaces. The associated run-off has a lesser degree of environmental impact (biochemical oxygen demand) on the ecosystem.

Room temperature ionic liquids composed wholly of naturally occurring ions were thought to be excellent candidates for deicing fluids. To prepare these ILs, a solution of choline chloride is dissolved in methanol and passed through an ion exchange resin to effect replacement of chloride with hydroxide. The resulting choline hydroxide solution is then reacted with a variety of naturally occurring carboxylic acids, including formic, acetic, propionic, butyric and amino acids including glycine and serine. The by-product water and solvent are removed by evaporative distillation to provide the pure ionic liquids. Many of the resulting ionic liquids are indeed liquid at room temperature. All are completely soluble in water. They show toxicity profiles that have lesser impact on the environment that some conventional deicing formulations.

Embodiments of the invention relate to a deicing composition and process for making a deicing composition. Aspects of the invention relate to a process for making deicing compositions including, dissolving a choline halogen salt(s) in at least one alcohol having the structure selected from the group consisting of alcohols having a $C_nH_{2n+1}OH$ structure where "n" is equal or greater than 1 and passing through an ion exchange resin (such as Amberlite® IRA-78) to produce a first solution of choline hydroxide, reacting the first solution with an organic acid(s) in an equimolar ratio to produce a second solution, and evaporative distilling the second solution to remove by-product including water and solvents to produce pure eco-friendly choline-based ionic liquids.

Other aspects of the invention relate to a pure eco-friendly choline-based ionic liquids deicing composition. Embodiments of the invention relates to a deicing composition including, at least one purified ionic liquid including choline having a composition that is environmentally friendly when utilized as a deicing composition, wherein the choline-based ionic liquid having choline salts selected from the group consisting of, but not limit to, choline formate, choline acetate, choline propionate, choline glycolate, choline tiglate, choline pivalate, choline pyruvate, and choline trifluoroacetate.

Embodiments of the invention relates to a deicing composition including, at least one purified ionic liquid including choline having a composition that is environmentally friendly when utilized as a deicing composition, wherein the choline-based ionic liquid having choline salts selected from the group consisting of, but not limited to, choline leucinate, choline isoleucinate, choline asparaginate, choline arginate, choline cysteinate, choline glutamate, choline histidinate, choline lysinate, choline methioninate, choline serinate, choline threoninate, choline tryptophanate, choline valinate, and choline tyrosinate.

Embodiments of the invention relates to a deicing composition including, at least one purified ionic liquid including choline having a composition that is environmentally friendly when utilized as a deicing composition, wherein the choline-based ionic liquid having choline salts selected from the group consisting of choline sulfamate, choline methylsulfate, and choline ethylsulfate. In embodiments, the halogen of the choline halogen salt(s) are selected from the group consisting of, but not limited to, fluoride, chloride, bromide, and iodide. In embodiments, the alcohol is selected from the group consisting of, but not limited to, ethanol, methanol, isomers of propanol, and butanol.

In embodiments, the organic acid(s) are carboxylic acids having at least one of, but not limited to, formic acids, acetic acids, propionic acids, butyric acids, amino acids, and any combination thereof. In other embodiments, the organic acids are monobasic alkyl-type selected from the group consisting of, but not limited to, formic, acetic, propionic, butyric, glycolic, tiglic, pivalic, lactic, pyruvic, and trifluoroacetic. Yet in other embodiments, the organic acids are dibasic alkyl-type selected from the group consisting of, but not limited to, tartaric, oxalic, succinic, maleic, fumaric, and malonic. Still yet in other embodiments, the organic acids are tribasic alkyl-type including, but not limited to, citric. Still in further embodiments, the organic acids are monobasic aryl-type selected from the group consisting of, but not limited to, benzoic and salicylic. In embodiments, the organic acids are of the naturally occurring amino acids selected from the group consisting of, but not limited to, glycine, proline, glutamine, glutaric, phenylalanine, leucine, isoleucine, asparagines, arginine, cysteine, glutamic acid, histidine, lysine, methionine, serine, threonine, tryptophan, valine and tyrosine; or sulfur-type acids: sulfamic, methylsulfate, and ethylsulfate.

In embodiments, the choline-based ionic liquids having choline salts are selected from the group consisting of choline formate, choline acetate, choline propionate, choline glycolate, choline tiglate, choline pivalate, choline pyruvate, and choline trifluoroacetate. In other embodiments, the choline-based ionic liquids having choline salts are selected from the group consisting of choline leucinate, choline isoleucinate, choline asparaginate, choline arginate, choline cysteinate, choline glutamate, choline histidinate, choline lysinate, choline methioninate, choline serinate, choline threoninate, choline tryptophanate, choline valinate, and choline tyrosinate. In still yet other embodiments, the choline-based ionic liquids having choline salts are selected from the group consisting of choline sulfamate, choline methylsulfate, and choline ethylsulfate.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for making deicing compositions, comprising:
   dissolving a choline halogen salt(s) in at least one alcohol having the structure selected from the group consisting of alcohols having a $C_nH_{2n+1}OH$ structure where "n" is equal or greater than 1 and passing through an ion exchange resin to produce a first solution of choline hydroxide;
   reacting said first solution with an organic acid(s) in an equimolar ratio to produce a second solution; and
   evaporative distilling said second solution to remove by-product including water and solvents to produce pure eco-friendly choline-based ionic liquids having deicing capabilities.

2. The process according to claim 1, wherein said halogen of said choline halogen salt(s) are selected from the group consisting of fluoride, chloride, bromide, and iodide.

3. The process according to claim 1, wherein said alcohol is selected from the group consisting of ethanol, methanol, isomers of propanol, and butanol.

4. The process according to claim 1, wherein said organic acid(s) are carboxylic acids having at least one of formic acids, acetic acids, propionic acids, butyric acids, amino acids, and any combination thereof.

5. The process according to claim 1, wherein said organic acids are monobasic alkyl-based selected from the group consisting of formic, acetic, propionic, butyric, glycolic, tiglic, pivalic, lactic, pyruvic, and trifluoroacetic.

6. The process according to claim 1, wherein said organic acids are dibasic alkyl-based selected from the group consisting of tartaric, oxalic, succinic, maleic, fumaric, and malonic.

7. The process according to claim 1, wherein said organic acids are tribasic alkyl-based.

8. The process according to claim 1, wherein said organic acids are monobasic aryl-based selected from the group consisting of benzoic and salicylic.

9. The process according to claim 1, wherein said organic acids are of the naturally occurring amino acids selected from the group consisting of glycine, proline, glutamine, glutaric, phenylalanine, leucine, isoleucine, asparagines, arginine, cysteine, glutamic acid, histidine, lysine, methionine, serine, threonine, tryptophan, valine and tyrosine; or sulfur-based acids.

10. The process according to claim 1, wherein said choline-based ionic liquids having choline salts selected from the group consisting of choline formate, choline acetate, choline propionate, choline glycolate, choline tiglate, choline pivalate, choline pyruvate, and choline trifluoroacetate.

11. The process according to claim 1, wherein said choline-based ionic liquids having choline salts selected from the group consisting of choline leucinate, choline isoleucinate, choline asparaginate, choline arginate, choline cysteinate, choline glutamate, choline histidinate, choline lysinate, choline methioninate, choline serinate, choline threoninate, choline tryptophanate, choline valinate, and choline tyrosinate.

12. The process according to claim 1, wherein said choline-based ionic liquids having choline salts selected from the group consisting of choline sulfamate, choline methylsulfate, and choline ethylsulfate.

13. The process according to claim 7 wherein said tribasic alkyl-based acid is citric acid.

14. The process according to claim 9 wherein said sulfur-based acids are selected from the group consisting of sulfamic, methylsulfate, and ethylsulfate.

* * * * *